US00PP27810P3

(12) United States Plant Patent
Meilland

(10) Patent No.: US PP27,810 P3
(45) Date of Patent: Mar. 28, 2017

(54) HYBRID TEA ROSE PLANT NAMED 'MEICEAZAR'

(50) Latin Name: *Rosa hybrida*
Varietal Denomination: Meiceazar

(71) Applicant: CP DELAWARE, INC., Wilmington, DE (US)

(72) Inventor: Alain A. Meilland, Antibes (FR)

( * ) Notice: Subject to any disclaimer, the term of this patent is extended or adjusted under 35 U.S.C. 154(b) by 8 days.

(21) Appl. No.: 14/545,302

(22) Filed: Apr. 21, 2015

(65) Prior Publication Data

US 2016/0249501 P1 Aug. 25, 2016

(30) Foreign Application Priority Data

Feb. 20, 2015 (QZ) ..... PBR 2015/0412

(51) Int. Cl.
*A01H 5/02* (2006.01)

(52) U.S. Cl.
USPC ..... Plt./140

(58) Field of Classification Search
USPC ..... Plt./140
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct Hybrid Tea rose plant is provided that forms abundantly and substantially continuously attractive very double blossoms which display a strong fragrance. The growth habit is bushy, and very strong vegetation is formed. The vegetation is dense and bears a semi-glossy aspect on the upper surface and contrasts nicely with the red blossom coloration. The disease tolerance is very good particularly with respect to black spot. The plant is well suited for providing attractive ornamentation in parks and gardens.

1 Drawing Sheet

Figures 1, 2, 3, 4, 5, 6, 7, 8, 9, 10, 11, 12, 13, 14, 15:
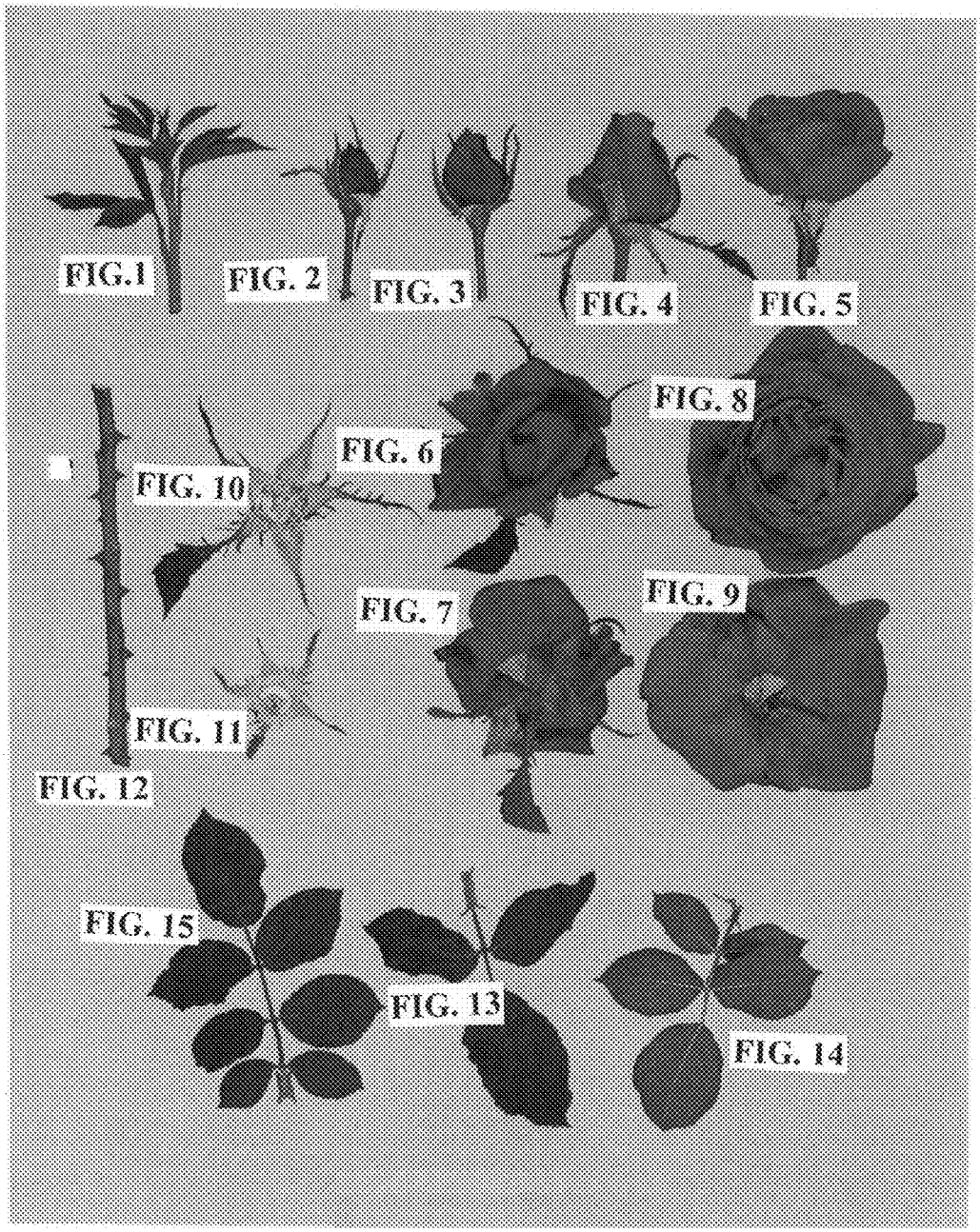

Botanical/commercial classification: *Rosa hybrida*/Hybrid Tea Rose Plant.

Varietal denomination: cv. Meiceazar.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meivilese' variety (non-patented in the United States) and 'Duc de Windsor' variety (non-patented in the United States). The male parent (i.e., the pollen parent) was the 'Deep Secret' variety (non-patented in the United States).

The parentage of the new variety can be summarized as follows:

('Meivilese'×'Duc de Windsor')×'Deep Secret'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a bushy growth habit with very strong vegetation,
(b) forms in abundance on a substantially continuous basis attractive very double pure red blossoms which display a strong fragrance,
(c) exhibits very dense semi-glossy dark green foliage that contrasts nicely with the red blossom coloration, (d) displays good disease tolerance particularly with respect to black spot, and
(e) is well suited for providing attractive ornamentation in parks and gardens.

The blooming tends to commence medium in the season, during observations to date.

The new variety well meets the needs of the horticultural industry and can be grown to advantage in the landscape where attractive ornamentation is to be provided.

The new variety can be readily distinguished from its ancestors. More specifically, the 'Meivilese' variety displays smaller foliage. When compared to the 'Duc de Windsor' and 'Deep Secret' varieties, the blossoms of the new variety display more petals. The female parent ('Meivilese'×'Duc de Windsor') has fewer petals than the new variety and is dark pink in coloration.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meiceazar'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during July while budded on *Rosa coriifolia* var. *froebelii* understock at Le Cannet des Maures, Var, France.

FIG. 1—illustrates a specimen of a young shoot;

FIG. 2—illustrates a specimen of floral bud at the opening of the sepals;

FIG. 3—illustrates a specimen of floral bud at the opening of the petals;

FIG. 4—illustrates a specimen of a flower in the course of opening.

FIG. 5—illustrates a specimen of a newly open flower—plan view—obverse;

FIG. 6—illustrates a specimen of an open flower—plan view—obverse;

FIG. 7—illustrates a specimen of a fully open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a leaf with three leaflets—plan view—upper surface;

FIG. 14—illustrates a specimen of a leaf with five leaflets—plan view—under surface; and FIG. 15—illustrates a specimen of a leaf with seven leaflets—plan view—upper surface.

DETAILED BOTANICAL DESCRIPTION

The chart used in the identification of the colors is that of The Royal Horticultural Society (R.H.S. Colour Chart). The description is based on the observation of one-year-old plants during July while budded on *Rosa coriifolia* var. *froebelii* understock and growing outdoors at Le Cannet des Maures, Var, France.

Class: Hybrid Tea.

Plant:

*Growth habit*.—Bushy.

*Height*.—Approximately 90-120 cm on average.

*Spread*.—Approximately 70-80 cm on average.

Branches:

*Stem size*.—Length: commonly approximately 45 cm on average; Diameter commonly approximately 1 cm on average.

*Color*.—Young stems: near Yellow-Green Group 146C. Adult wood: near Yellow-Green Group 146B.

*Thorns*.—On young stems: Configuration: with an oval base. Small prickles: Quantity: commonly 8 on average over a stem length of 10 cm. Length: approximately 1 mm on average. Color: near Greyed-Orange Group 174C. Long prickles: Configuration: with an oval base. Quantity: approximately 5 on average on a stem length of 10 cm. Length: approximately 5 mm on average. Color: near Greyed-Orange Group 174C. On adult stems: Small prickles: Configuration: slightly curved downwards on the upper surface and concave on the under surface with an oval base. Quantity: approximately 1 on average over a stem length of 10 cm. Length: approximately 2 mm on average. Color: near Greyed-Orange Group 164C. Long prickles: Configuration: slightly curved downwards on the upper surface and concave on the under surface with an oval base. Quantity: approximately 7 on average on a stem length of 10 cm. Length: approximately 7 mm on average, Color: near Greyed-Orange Group 164C.

Leaves:

*Size*.—Overall size of a 5-leaflet leaf: Length: approximately 11 cm on average; width: approximately 8 cm on average.

*Stipules*.—Adnate, pectinate, rather broad, approximately 1.8 cm in length on average, approximately 0.6 cm in width on average, near Yellow-Green Group 148C on the upper surface, and near Yellow-Green Group 146D on the under surface.

*Petioles*.—Upper surface: near Yellow-Green Group 146A in coloration. Under surface: near Yellow-Green Group 146C in coloration. Length: approximately 3 cm on average for the terminal leaflet. Diameter: approximately 0.6-0.7 mm on average. Texture: non-glandular on the upper surface, and commonly with a few prickles on the under surface.

*Rachis*.—Upper surface: near Yellow-Green Group 152C in coloration. Under surface: near Yellow-Green Group 146C in coloration. Length: approximately 3 cm on average. Diameter: approximately 4 mm on average.

*Leaflets*.—Number: 3, and most often 5 and 7. Shape: generally oval with an acuminate tip and an obtuse base, Size: the terminal leaflets commonly are approximately 7.5 cm in length on average and approximately 4.5 to 6 cm in width on average. Edges: slightly denticulate. Serration: small and single as illustrated). Texture: physically firm and leathery. Color (young foliage): Upper surface: near Yellow-Green Group 147B. Under surface: near Yellow-Green Group 148B. Color (adult foliage): Upper surface: near Yellow-Green Group 146A. Under surface: near Yellow-Green Group 146B.

Inflorescence:

*Number of flowers*.—Commonly 1 blossom per stem.

*Peduncle*.—Commonly pubescent, approximately 6 cm in length on average, approximately 4 mm in diameter on average, and near Yellow-Green Group 146C with some anthocyanin coloration near Greyed-Purple Group 178A in coloration.

*Sepals*.—Upper surface: tomentose and near Yellow-Green Group 147C in coloration. Under surface: smooth and near Yellow-Green Group 146C in coloration. Shape: longish and narrow, and somewhat upright at the base. Size: approximately 3.5 cm in length on average, and approximately 1 cm in width at the widest point on average.

*Buds*.—Shape: substantially conical. Size: large. Length: approximately 3.2 cm on average. Width: approximately 2.9 cm at the widest point on average. Color as calyx breaks: near Red Group 46A commonly suffused with darker than Red Group 53A on the upper surface, and near Red Group 53A on the under surface.

*Flower*.—Shape: cup-shaped. Diameter: approximately 12 cm on average. Depth: approximately 7-8 cm on average. Color (in the course of opening): Upper surface: near Red Group 46A commonly suffused with darker than Red Group 53A. Under surface: near Red Group 53A. Color (open flower):

Upper side: near Red Group 46A commonly suffused with darker than Red Group 53B. Under side: near Red Group 53B. Fragrance: strong. Petal number: approximately 45 on average under normal growing conditions. Petal shape: with a substantially rounded tip and an obtuse base. Petal texture: leathery and somewhat firm. Petal length: approximately 6 cm on Average. Petal width: approximately 6.5 to 7 cm on average. Petal arrangement: imbricated, and without petaloids. Petal drop: good with the petals commonly detaching cleanly before drying. Stamen number: approximately 158 on average. Anthers: regularly arranged around the styles, approximately 3 mm in length and 1 mm in diameter on average, and near Yellow-Orange Group 22A in coloration. Filaments: approximately 4 to 7 mm in length on average, and near Red Group 45A in coloration. Pollen: none available for observation. Pistils: approximately 95 on average. Stigmas: approximately 1 mm in length and 1 mm in diameter on average, and near Red Group 45B in coloration. Styles: approximately 5 mm in length on average, and near Yellow Group 2D in coloration. Receptacle: smooth, funnel-shaped in longitudinal section, approximately 8 mm in length on average, approximately 1.3 cm in width on average at the widest point, and near Yellow-Green Group 146C in coloration.

Development:

*Vegetation*.—Very strong.

*Blooming*.—Medium season, very abundant and substantially continuous.

*Tolerance to Diseases*.—Good particularly with respect to black spot.

The new 'Meiceazar' variety has not been observed under all possible environmental conditions to date. Accordingly, it is possible that the phenotypic expression may vary somewhat with changes in light intensity and duration, cultural practices, and other environmental conditions.

I claim:

1. A new and distinct Hybrid Tea rose plant characterized by the following characteristics:

(a) displays a bushy growth habit with very strong vegetation, (b) forms in abundance on a substantially continuous basis attractive very double pure red blossoms which display a strong fragrance, (c) exhibits very dense semi-glossy dark green foliage that contrasts nicely with the red blossom coloration, (d) displays good tolerance to disease particularly with respect to black spot, and (e) is well suited for providing attractive ornamentation in parks and gardens;

substantially as shown and described.

* * * * *